United States Patent
Butler

(10) Patent No.: US 7,591,784 B2
(45) Date of Patent: Sep. 22, 2009

(54) BI-DIRECTIONAL HANDLE FOR A CATHETER

(75) Inventor: William Emerson Butler, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 871 days.

(21) Appl. No.: 11/115,600

(22) Filed: Apr. 26, 2005

(65) Prior Publication Data
US 2006/0253070 A1    Nov. 9, 2006

(51) Int. Cl.
*A61B 1/01*   (2006.01)
*A61M 31/00*  (2006.01)

(52) U.S. Cl. .............................. 600/146; 606/1; 606/41; 604/95.04

(58) Field of Classification Search ................. 600/146, 600/149, 585; 604/95.04, 528; 606/1, 41
See application file for complete search history.

(56) References Cited

U.S. PATENT DOCUMENTS

| | | | | |
|---|---|---|---|---|
| 4,941,455 A | * | 7/1990 | Watanabe et al. ........... 600/146 |
| 4,960,134 A | | 10/1990 | Webster, Jr. ................. 128/786 |
| 4,986,257 A | * | 1/1991 | Chikama ..................... 600/146 |
| 5,125,895 A | | 6/1992 | Buchbinder et al. ........... 604/95 |
| 5,125,896 A | | 6/1992 | Hojeibane .................... 604/95 |
| 5,269,757 A | | 12/1993 | Fagan et al. .................. 604/95 |
| RE34,502 E | | 1/1994 | Webster, Jr. ................. 607/125 |
| 5,277,199 A | | 1/1994 | DuBois et al. ............... 128/772 |
| 5,281,217 A | | 1/1994 | Edwards et al. .............. 606/41 |
| 5,318,525 A | | 6/1994 | West et al. ................... 604/95 |
| 5,327,889 A | | 7/1994 | Imran ......................... 128/642 |
| 5,327,905 A | | 7/1994 | Avitall ........................ 128/772 |
| 5,327,906 A | | 7/1994 | Fideler et al. | |
| 5,330,466 A | | 7/1994 | Imran ......................... 606/13 |
| 5,342,295 A | | 8/1994 | Imran ......................... 604/43 |
| 5,354,297 A | | 10/1994 | Avitall ........................ 606/45 |
| 5,364,351 A | | 11/1994 | Heinzelman et al. | |
| 5,383,923 A | | 1/1995 | Webster, Jr. ................. 607/125 |

(Continued)

FOREIGN PATENT DOCUMENTS

EP    1 205 208    5/2002

(Continued)

*Primary Examiner*—John P Leubecker
(74) *Attorney, Agent, or Firm*—Dykema Gossett LLP

(57) ABSTRACT

A catheter actuation handle for deflecting a distal end of a tubular catheter body having first and second actuation wires extending from a proximal end of the body. The handle comprises a first grip portion, a bearing assembly, and an actuator. The first grip portion includes a pivot with a pathway extending through the pivot. The pathway is generally parallel to a longitudinal centerline of the first grip portion. The bearing assembly is located on the first grip portion proximal to the pivot. The actuator is pivotally coupled to the pivot and includes first and second ends that are laterally offset from the longitudinal centerline and are on opposite sides of the centerline from each other. When the distal end of the handle is coupled to the proximal end of the body, the first and second actuation wires extend along the pathway to the bearing assembly. The bearing assembly diverts the first actuation wire to a first connection point on the actuator and the second actuation wire to a second connection point on the actuator.

41 Claims, 3 Drawing Sheets

U.S. PATENT DOCUMENTS

| | | | | |
|---|---|---|---|---|
| 5,389,073 | A | 2/1995 | Imran | 604/95 |
| 5,391,147 | A | 2/1995 | Imran et al. | 604/95 |
| 5,395,328 | A | 3/1995 | Ockuly et al. | 604/95 |
| 5,395,329 | A | 3/1995 | Fleischhacker et al. | 604/95 |
| 5,397,304 | A | 3/1995 | Truckai | 604/95 |
| 5,431,168 | A | 7/1995 | Webster, Jr. | 128/658 |
| 5,445,148 | A | 8/1995 | Jaraczewski et al. | 128/642 |
| 5,478,330 | A | 12/1995 | Imran et al. | 604/282 |
| 5,487,385 | A | 1/1996 | Avitall | 128/642 |
| 5,487,757 | A | 1/1996 | Truckai et al. | 607/122 |
| 5,527,279 | A | 6/1996 | Imran | 604/95 |
| 5,533,967 | A | 7/1996 | Imran | 604/95 |
| 5,545,200 | A | 8/1996 | West et al. | 607/122 |
| 5,562,619 | A | 10/1996 | Mirarchi et al. | 604/95 |
| 5,582,609 | A | 12/1996 | Swanson et al. | 606/39 |
| 5,588,964 | A | 12/1996 | Imran et al. | 604/95 |
| 5,611,777 | A | 3/1997 | Bowden et al. | 604/95 |
| 5,626,136 | A | 5/1997 | Webster, Jr. | 128/642 |
| 5,656,029 | A | 8/1997 | Imran et al. | 604/95 |
| 5,656,030 | A | 8/1997 | Hunjan et al. | 604/95 |
| 5,755,760 | A | 5/1998 | Maguire et al. | 607/122 |
| 5,779,669 | A | 7/1998 | Haissaguerre et al. | 604/95 |
| 5,807,249 | A | 9/1998 | Qin et al. | 600/374 |
| 5,826,576 | A | 10/1998 | West | 128/642 |
| 5,827,272 | A | 10/1998 | Breining et al. | 606/41 |
| 5,827,278 | A | 10/1998 | Webster | 606/41 |
| 5,836,947 | A | 11/1998 | Fleischman et al. | 606/47 |
| 5,842,984 | A | 12/1998 | Avitall | 600/374 |
| 5,843,031 | A | 12/1998 | Hermann et al. | 604/95 |
| 5,843,076 | A | 12/1998 | Webster, Jr. et al. | 606/41 |
| 5,861,024 | A | 1/1999 | Rashidi et al. | |
| 5,865,800 | A | 2/1999 | Mirarchi et al. | 604/95 |
| 5,885,278 | A | 3/1999 | Fleischman et al. | 606/41 |
| 5,897,529 | A | 4/1999 | Ponzi | 604/95 |
| 5,910,129 | A | 6/1999 | Koblish et al. | 604/95 |
| 5,916,213 | A | 6/1999 | Haissaguerre et al. | 606/41 |
| 5,916,214 | A | 6/1999 | Cosio et al. | 606/41 |
| 5,921,924 | A | 7/1999 | Avitall | 600/374 |
| 5,931,811 | A | 8/1999 | Haissaguerre et al. | 604/95 |
| 5,935,102 | A | 8/1999 | Bowden et al. | 604/95 |
| 5,944,690 | A | 8/1999 | Falwell et al. | 604/95 |
| 5,960,145 | A * | 9/1999 | Sanchez | 385/116 |
| 5,987,344 | A | 11/1999 | West | 600/373 |
| 5,993,462 | A | 11/1999 | Pomeranz et al. | 606/129 |
| 6,002,955 | A | 12/1999 | Willems et al. | 600/374 |
| 6,024,722 | A | 2/2000 | Rau et al. | |
| 6,027,473 | A | 2/2000 | Ponzi | 604/95 |
| 6,033,403 | A | 3/2000 | Tu et al. | 606/41 |
| 6,048,329 | A | 4/2000 | Thompson et al. | 604/95 |
| 6,059,739 | A | 5/2000 | Baumann | 600/585 |
| 6,064,902 | A | 5/2000 | Haissaguerre et al. | 600/381 |
| 6,066,125 | A | 5/2000 | Webster, Jr. | 604/528 |
| 6,068,629 | A | 5/2000 | Haissaguerre et al. | 606/41 |
| 6,071,274 | A | 6/2000 | Thompson et al. | 604/528 |
| 6,071,279 | A | 6/2000 | Whayne et al. | 606/41 |
| 6,071,282 | A | 6/2000 | Fleischman | 606/41 |
| 6,083,222 | A | 7/2000 | Klein et al. | 606/41 |
| 6,090,104 | A | 7/2000 | Webster, Jr. | 606/41 |
| 6,123,699 | A | 9/2000 | Webster, Jr. | 604/528 |
| 6,138,043 | A | 10/2000 | Avitall | 600/377 |
| 6,149,663 | A | 11/2000 | Strandberg et al. | 606/180 |
| 6,156,034 | A | 12/2000 | Cosio et al. | 606/41 |
| 6,169,916 | B1 | 1/2001 | West | 600/373 |
| 6,171,277 | B1 | 1/2001 | Ponzi | 604/95.04 |
| 6,178,354 | B1 | 1/2001 | Gibson | 607/116 |
| 6,183,435 | B1 | 2/2001 | Bumbalough et al. | 604/95.01 |
| 6,183,463 | B1 | 2/2001 | Webster, Jr. | 604/528 |
| 6,198,974 | B1 | 3/2001 | Webster, Jr. | 607/122 |
| 6,200,315 | B1 | 3/2001 | Gaiser et al. | 606/41 |
| 6,203,507 | B1 | 3/2001 | Wadsworth et al. | 600/585 |
| 6,203,525 | B1 | 3/2001 | Whayne et al. | 604/95.01 |
| 6,210,362 | B1 | 4/2001 | Ponzi | 604/95.01 |
| 6,210,407 | B1 | 4/2001 | Webster | 606/41 |
| 6,214,002 | B1 | 4/2001 | Fleischman et al. | 606/41 |
| 6,221,087 | B1 | 4/2001 | Anderson et al. | 606/159 |
| 6,224,587 | B1 | 5/2001 | Gibson | 604/528 |
| 6,241,754 | B1 | 6/2001 | Swanson et al. | 607/99 |
| 6,308,091 | B1 | 10/2001 | Avitall | 600/374 |
| 6,375,654 | B1 | 4/2002 | McIntyre | 606/41 |
| 6,430,426 | B2 | 8/2002 | Avitall | 600/374 |
| 6,454,758 | B1 | 9/2002 | Thompson et al. | 604/528 |
| 6,582,536 | B2 | 6/2003 | Shimda | |
| 7,025,759 | B2 * | 4/2006 | Muller | 604/528 |
| 2001/0025134 | A1 * | 9/2001 | Bon et al. | 600/146 |
| 2003/0092965 | A1 * | 5/2003 | Konomura et al. | 600/146 |
| 2003/0109778 | A1 * | 6/2003 | Rashidi | 600/374 |
| 2003/0135199 | A1 * | 7/2003 | Rosenman et al. | 604/528 |
| 2006/0084964 | A1 * | 4/2006 | Knudson et al. | 606/41 |
| 2006/0142695 | A1 * | 6/2006 | Knudson | 604/95.04 |
| 2008/0255540 | A1 * | 10/2008 | Selkee | 604/528 |

FOREIGN PATENT DOCUMENTS

GB    1 170 018    11/1969

* cited by examiner

US 7,591,784 B2

BI-DIRECTIONAL HANDLE FOR A CATHETER

FIELD OF THE INVENTION

The present invention relates to catheters and sheaths and methods of using catheters and sheaths. More particularly, the present invention relates to steerable catheter or sheath control handles and methods of manufacturing and using such handles.

BACKGROUND OF THE INVENTION

Catheters having conductive electrodes along a distal end are commonly used for intra-cardiac electrophysiology studies. The distal portion of such a catheter is typically placed into the heart to monitor and/or record the intra-cardiac electrical signals during electrophysiology studies or during intra-cardiac mapping. The orientation or configuration of the catheter distal end is controlled via an actuator located on a handle outside of the body, and the electrodes conduct cardiac electrical signals to appropriate monitoring and recording devices that are operatively connected at the handle of the catheter.

Typically, these catheters include a generally cylindrical electrically non-conductive body. The main body includes a flexible tube constructed from polyurethane, nylon or other electrically non-conductive flexible material. The main body further includes braided steel wires or other non-metallic fibers in its wall as reinforcing elements. Each electrode has a relatively fine electrically conductive wire attached thereto and extending through the main body of the catheter. The conductive wire extends from the distal end to a proximal end where electrical connectors such as plugs or jacks are provided to be plugged into a corresponding socket provided in a recording or monitoring device.

The distal portion of the main body is selectively deformed into a variety of curved configurations using the actuator. The actuator is commonly internally linked to the distal portion of the catheter by at least one actuation wire. Some catheters employ a single actuation wire, which is pulled (i.e., placed in tension) by the actuator in order to cause the distal portion of the main body to deform. Other catheters have at least two actuation wires, where the actuation of one wire (i.e., placing one wire in tension) results in the other wire going slack (i.e., the wire does not carry a compressive load). In such catheters, where the actuation wires are not adapted to carry compressive loads (i.e., the actuation wires are only meant to be placed in tension), the actuation wires are commonly called pull or tension wires.

To deform the distal end of the catheter into a variety of configurations, a more recent catheter design employs a pair of actuation wires that are adapted such that one of the actuation wires carries a compressive force when the other actuation wire carries a tensile force. In such catheters, where the actuation wires are adapted to carry both compressive and tension loads, the actuation wires are commonly called push/pull or tension/compression wires and the corresponding catheter actuators are called push-pull actuators. U.S. Pat. No. 5,861,024 to Rashidi, which issued Jan. 19, 1999, is representative of a push-pull actuator of this type, and the details thereof are incorporated herein by reference.

While many of the existing catheter actuators provide precise operation and good flexibility in movement of the distal portion of the body, the existing actuators often offer a range of distal portion displacement that is less than desirable. In other words, the amount of push/pull of the actuation wires (i.e., the steering travel) is often inadequate for the medical procedure being performed. The inadequacy of the steering travel typically results from the generally limited size of the actuator body, which is usually sized for receipt and manipulation between the thumb and index finger of a user's hand. Accordingly, a need exists to provide an improved actuating assembly for a catheter that increases the amount of steering travel associated with the actuator.

SUMMARY OF THE INVENTION

The present invention, in one embodiment, is a catheter actuation handle for deflecting a distal end of a tubular catheter body having first and second actuation wires extending from a proximal end of the body. The handle comprises a first grip portion, a bearing assembly, and an actuator. The first grip portion includes a pivot with a pathway extending through the pivot. The pathway is generally parallel to a longitudinal centerline of the first grip portion. The bearing assembly is located on the first grip portion proximal to the pivot. The actuator is pivotally coupled to the pivot and includes first and second ends that are laterally offset from the longitudinal centerline and are on opposite sides of the centerline from each other. When the distal end of the handle is coupled to the proximal end of the body, the first and second actuation wires extend along the pathway to the bearing assembly. The bearing assembly diverts the first and second actuation wires to respective first and second connection points on the actuator.

In one embodiment, the first connection point is near the first end and the second connection point is near the second end. In one embodiment, the bearing assembly changes the orientation of the actuation wires from an orientation that is generally parallel to the longitudinal centerline to an orientation that is generally non-parallel (e.g., oblique and/or perpendicular) to the longitudinal centerline. In one embodiment, the actuation wires cross the longitudinal centerline as they divert about the bearing assembly and travel to their respective connection points on the actuator.

In one embodiment, the first grip portion further includes a first generally planar area from which the pivot extends generally perpendicularly. The actuator further includes a first plate that is displaceable through a first space defined between the first generally planar area and a longitudinal axis of the pathway.

In one embodiment, the handle also includes a second grip portion mated with the first grip portion and including a second generally planar area. The actuator further includes a second plate that is coupled to the first plate and is displaceable through a second space defined between the second generally planar area and the longitudinal axis of the pathway.

In one embodiment, the first and second plates are generally parallel to each other and define a slot through which the actuation wires pass as the actuation wires extend from the pathway to the bearing assembly. In one embodiment, the bearing assembly further includes a portion that extends into the slot.

In one embodiment, the bearing assembly further includes a first bearing positioned on a first side of the longitudinal centerline and a second bearing positioned opposite the longitudinal centerline from the first bearing. In one embodiment, the bearings are annulus shaped. The first actuation wire diverts about the first bearing and the second actuation wire diverts about the second bearing. The bearing assembly further includes a separating assembly for separating the actuation wires into separate planes and the bearings are on opposite sides of the separating assembly from each other.

The present invention, in one embodiment, is a catheter actuation handle for deflecting a distal end of a tubular catheter body having first and second actuation wires extending from a proximal end of the body. The handle comprises a grip portion, a bearing assembly and an actuator. The grip portion includes a pivot and a longitudinal centerline. The bearing assembly is located on the grip portion proximal to the pivot. The actuator is pivotally coupled to the pivot and includes first and second ends that are laterally offset from the longitudinal centerline and are on opposite sides of the centerline from each other. When the distal end of the handle is coupled to the proximal end of the body, the first and second actuation wires extend along the grip portion towards the bearing assembly in a first orientation that is generally parallel to the longitudinal centerline. The bearing assembly is adapted to change the first orientation to a second orientation that is generally non-parallel (e.g., oblique and/or perpendicular) to the longitudinal centerline as the bearing assembly diverts the first and second actuation wires to respective first and second connection points on the actuator.

In one embodiment, the first connection point is near the first end and the second connection point is near the second end. In one embodiment, the actuation wires cross the longitudinal centerline as they divert about the bearing assembly and travel to their respective connection points on the actuator.

The present invention, in one embodiment, is a method of deflecting a distal end of a tubular catheter body having first and second actuation wires and coupled at a proximal end to an actuation handle. The method comprises diverting the first and second actuation wires about a bearing assembly of a grip portion of the handle and pivoting an actuator about a pivot of the grip portion, wherein the pivot is distal to the bearing assembly. In diverting the actuation wires, the orientation of each actuation wire changes from a first orientation that is generally parallel to a longitudinal centerline of the grip portion to a second orientation that is oblique to the longitudinal centerline. In pivoting the actuator, the first actuation wire is placed into tension.

In one embodiment, the first and second actuation wires are routed through a pathway in the pivot, wherein the pathway is generally parallel to the longitudinal centerline. In one embodiment, the actuation wires are also routed through a slot defined in the actuator after leaving the proximal end of the body, but prior to reaching the bearing assembly. Additionally, in one embodiment, the actuation wires are routed through the slot after leaving the bearing assembly for the actuator. Finally, in one embodiment, each actuation wire is caused to cross from one side of the longitudinal centerline to another when being diverted about the bearing assembly.

The present invention, in one embodiment, is a method of manufacturing a catheter with an actuation handle. The method comprises providing a grip portion of the handle with a pivot, and forming in the pivot a pathway that is generally parallel with a longitudinal centerline of the grip portion. Furthermore the method comprises placing a bearing assembly on the grip portion proximal to the pivot, pivotally mounting an actuator on the pivot, and routing first and second actuation wires through the pathway, about the bearing assembly, and to the actuator.

In one embodiment, the method further comprises changing the actuation wires from a first orientation that is generally parallel to the longitudinal centerline to a second orientation that is oblique to the centerline when routing the actuation wires about the bearing assembly. Also, in one embodiment, the method includes causing each actuation wire to cross from one side of the longitudinal centerline to another when routing the actuation wires about the bearing assembly. Finally, in one embodiment, the method includes routing the actuation wires from the pathway to the bearing assembly in a slot defined in the actuator.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION OF THE INVENTION

Figure 1:
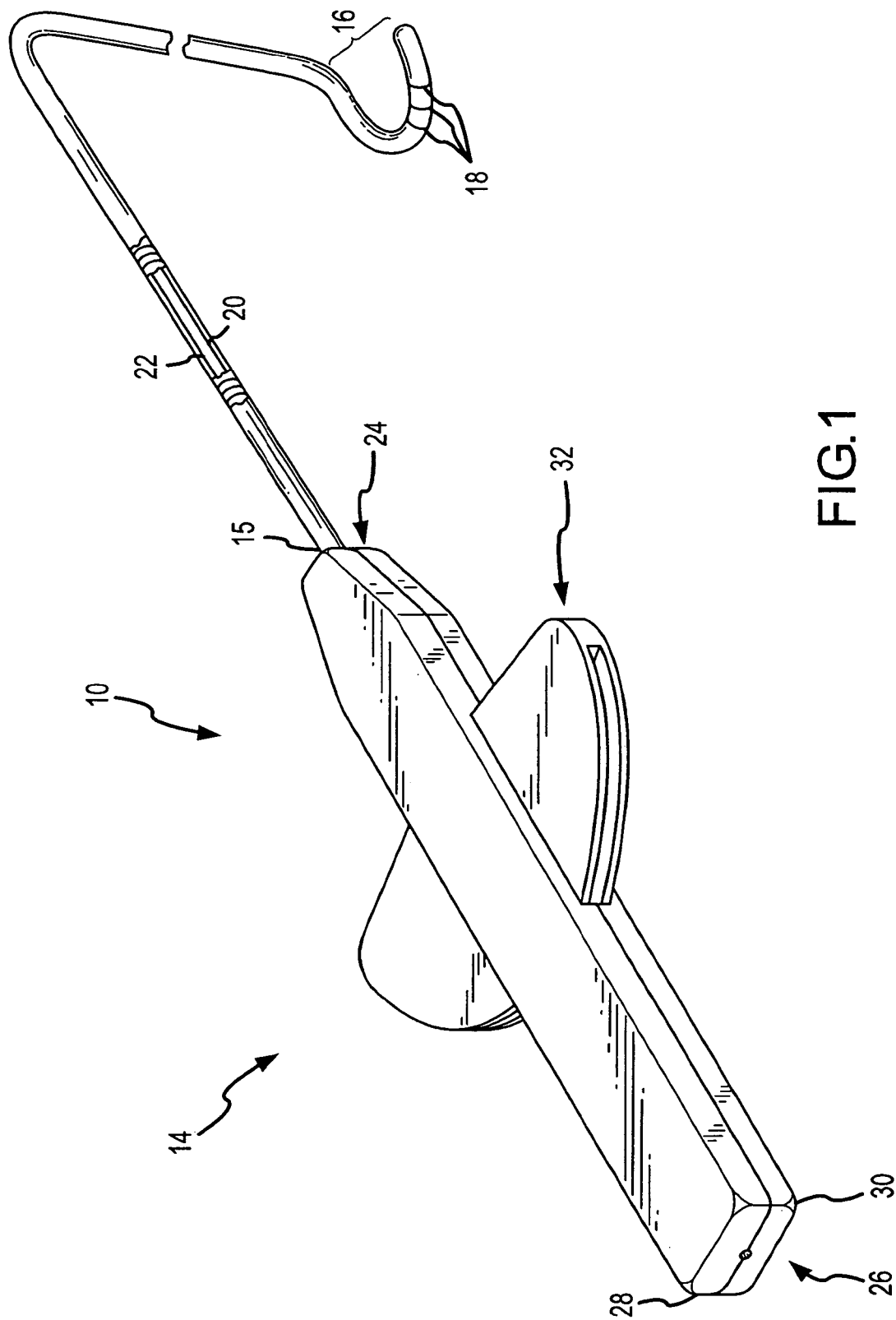
FIG. 1 is a perspective view of the catheter or sheath of the present invention with portions of the catheter's cylindrical hollow body broken away to show internal components of the body.

FIG. 1 is a perspective view of the catheter or sheath 10 of the present invention with portions of the catheter's elongated flexible generally cylindrical hollow body 12 broken away to show internal components of the body 12. As shown in FIG. 1, in one embodiment, the catheter 10, which is an electrophysiology, RF ablation, or similar catheter 10, includes an elongated flexible generally cylindrical hollow body 12 and an actuation handle 14 coupled to a proximal end 15 of the body 12. As will be understood from the following discussion, the catheter 10 is advantageous in that the actuation handle 14 is configured to significantly increase the steering travel of the distal end 16 of the body 12, as compared to prior art actuation handles.

In one embodiment, the body 12 is typically polyurethane, nylon or any suitable electrically non-conductive material. The body 12 serves as at least a portion of the blood-contacting segment of the catheter 10 and is vascularly inserted into a patient by methods and means well known in the art.

As illustrated in FIG. 1, the distal end 16 of the body 12 includes plural spaced electrodes 18. Each electrode 18 is connected to a fine electrical conductor wire that extends through the body 12 and the handle 14. An electrical plug extends from the proximal end of the handle 14 and is adapted to be inserted into a recording, monitoring, or RF ablation device.

As indicated in FIG. 1, the body 1-2 includes actuation wires 20, 22 that extend longitudinally in a side-by side relationship through the body 12 and into the handle 14. The handle 14 is used to displace the actuation wires 20, 22 to manipulate the distal end 16 of the body 12 into a variety of configurations and shapes to perform intravascular testing and ablation procedures. The distal ends of the actuation wires 20, 22 are coupled to the distal end 16 of the body 12, and the proximal end of the actuation wires 20, 22 are coupled to the handle's actuation mechanism.

In one embodiment, the actuation wires 20, 22 are formed from a super elastic Nitinol wire or another suitable material. In one embodiment, the actuation wires 20, 22 have a generally flat cross section, a circular cross section, or a combination of cross-sectional shapes along their length. For example, in one embodiment, the actuation wires 20, 22 are generally circular in cross-section along a substantial portion of the wire and have a flattened ribbon-like portion near the distal end 16 of the body 12.

In one embodiment, each actuation wire 20, 22 resides in a lumen or tube that runs generally the full length of the body 12 and helps to guide the actuation wire 20, 22 and prevent the actuation wire 20, 22 from buckling. In one embodiment, the actuation wires 20, 22 are pull or tension wires 20, 22 (i.e., the actuation wires 20, 22 are not adapted to support a compressive load). In another embodiment, the actuation wires 20, 22 and the lumens are configured such that the actuation wires 20, 22 are pull/push or tension/compression wires 20, 22 (i.e., the actuation wires 20, 22 are adapted to support a compressive load). Thus, when one actuation wire 20, 22 is placed in tension, the other actuation wire 20, 22 will carry a compressive load. This is advantageous because it allows for a decreased number of catheter components and increased deflection control of the distal end 16 of the body 12.

As shown in FIG. 1, the actuation handle 14 includes a distal end 24 coupled to the proximal end 15 of the body, a proximal end 26, an upper grip portion 28 coupled to a lower grip portion 30, and an actuation mechanism that includes an actuator 32 movably mounted to the grip portions 28, 30. As can be understood from FIG. 1, an operator can manipulate the distal end 16 of the body 12 by selectively moving the actuator 32 relative to the grip portions 28, 30.

As illustrated in FIG. 1, in one embodiment, the actuation handle 14 has a generally elongated rectangular shape. In other embodiments, the actuation handle 14 will employ other configurations without departing from the scope and intent of the invention.

Figure 2:
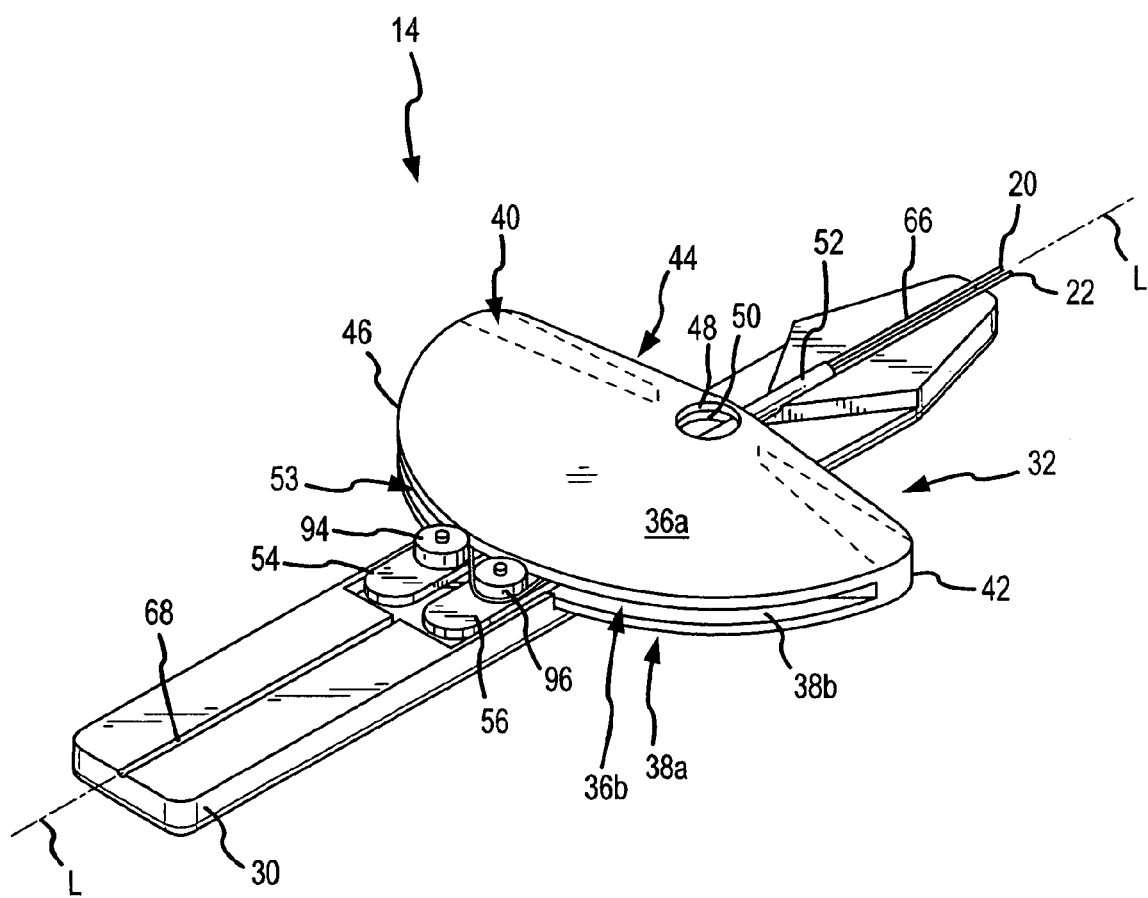
FIG. 2 is a perspective view of the actuator handle wherein the upper grip portion has been removed to reveal the actuation mechanism.

For a detailed discussion of the handle's actuator 32 and its relationship to other portions of the actuation mechanism 34 and the grip portions 28, 30, reference is now made to FIG. 2. FIG. 2 is a perspective view of the actuator handle 14 wherein the upper grip portion 28 has been removed to reveal the actuation mechanism 34. As shown in FIG. 2, in one embodiment, the actuator 32 includes a top plate 36, a bottom plate 38, and ribs 40, 42 (shown in phantom lines). Each plate 36, 38 has an outer planar surface 36*a*, 38*a* and an inner planar surface 36*b*, 38*b*. The actuator 32 is configured such that the inner planar surfaces 36*b*, 38*b* are opposed and generally parallel to each other.

As illustrated in FIG. 2, in one embodiment, the actuator 32 is generally semi-circular in shape such that the actuator 32 has a distal generally linear side or edge 44 and a proximal generally arcuate side or edge 46 that extends between the ends of the generally linear side or edge 44. As indicated in FIG. 2, in one embodiment, each plate 36, 38 includes a pivot hole 48, 50 that is located near, and centered along, the linear side 44. In one embodiment, the radius of the arcuate side 46 is generally measured from the center of the pivot holes 48, 50.

As indicated in FIG. 2, the ribs 40, 42 are generally perpendicular to, and extend between, the inner planar surfaces 36*b*, 38*b* to interconnect the plates 36, 38 to each other to form an integral actuator 32. As illustrated via phantom lines in FIG. 2, in one embodiment, the ribs 40, 42 extend from their respective ends of the linear side 44 towards the pivot holes 48, 50. The ribs 40, 42 are configured such that the actuator may pivot about the pivot holes 48, 50 and relative to the grip portions 28, 30 without abutting against a wire guide 52 and the actuation wires 20, 22, which pass generally perpendicularly through the axis of the pivot holes 48, 50, as described later in this Detailed Description. For example, as indicated in FIG. 2 by phantom lines, to provide adequate clearance for actuator pivoting, the ribs 40, 42 terminate prior to reaching the pivot holes 48, 50. Additionally, the ribs 40, 42 taper down as they extend towards the pivot holes 48, 50 such that the linear sides or edges 44 of each plate 36, 38 extend distally past the ribs 40, 42 (i.e., the ribs 40, 42 are recessed relative to the linear sides or edges 44 of each plate).

As shown in FIG. 2, a slot 53 in the actuator 32 is defined between the inner planar surfaces 36*b*, 38*b*. The slot 53 extends distally from the arcuate side 46 of the actuator 32 towards the ribs 40, 42. As the actuator 32 is pivoted relative to the grip portions 28, 30, the slot 53 allows the upper and lower plates 36, 38 to pass over and under, respectively, the actuation wires 20, 22, the wire guide 52, and the distal ends of a pair of wire dividers 54, 56, as will now be described in the following discussion of FIG. 3.

Figure 3:
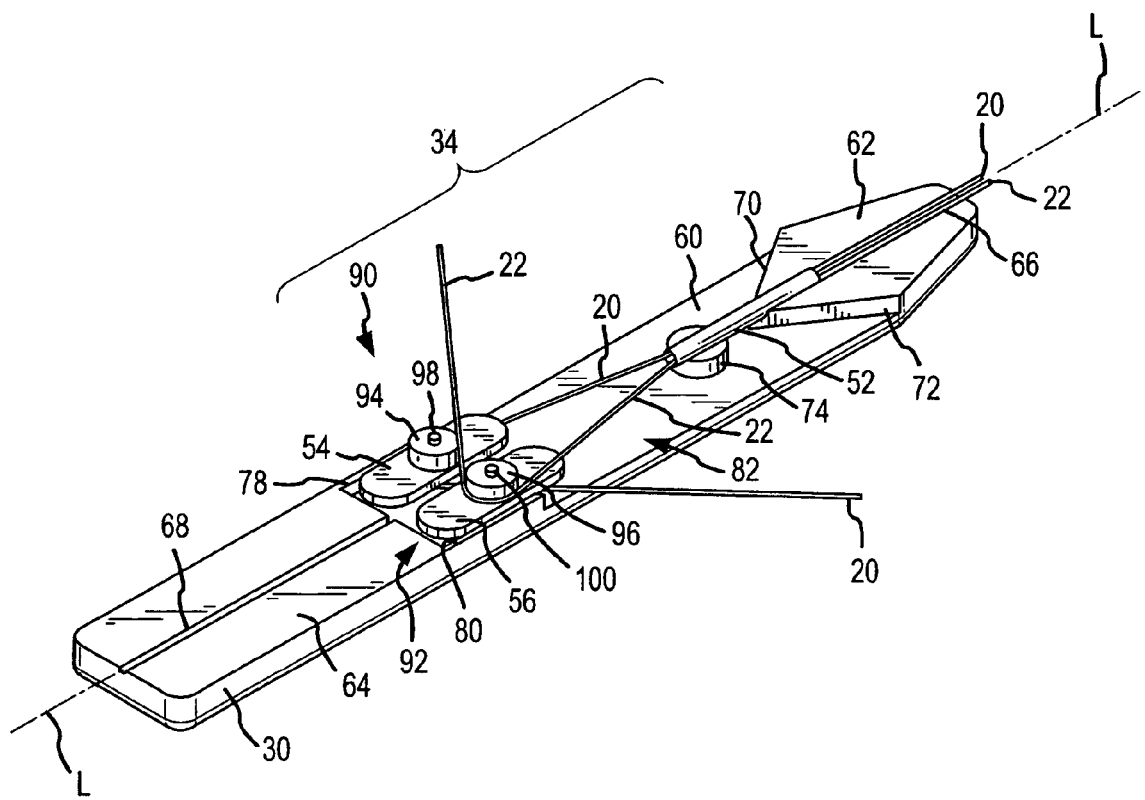
FIG. 3 is the same view of the handle depicted in FIG. 2, except the actuator has been removed to more fully illustrate the rest of the actuation mechanism.

FIG. 3 is the same view of the handle depicted in FIG. 2, except the actuator 32 has been removed to more fully illustrate the rest of the actuation mechanism 34. As illustrated in FIG. 3, in one embodiment, the lower grip portion 30, which is generally a mirror image of the upper grip portion 28 (i.e., the discussion of the features of the lower grip portion 30 is generally equally applicable to the features of the upper grip portion 28), includes a recessed planar area 60 defined between a distal planar area 62 and a proximal planar area 64. A distal groove 66 extends through the distal planar area 62 along the longitudinal centerline L of the lower grip portion 30. Similarly, a proximal groove 68 extends through the proximal planar area 64 along the longitudinal centerline L of the lower grip portion 30. When the upper and lower grip portions 28, 30 are mated together to form the handle 14, the distal and proximal planar areas 62, 64 of the upper grip portion 28 matingly abut against their respective planar areas 62, 64 of the lower grip portion 30, and the grooves 66, 68 in each grip portion 28, 30 combine to form a channel, lumen or pathway that, in one embodiment, is coaxial with the longitudinal axis of the handle 14 and extends through the handle 14.

For example, as indicated in FIG. 3, the distal groove 66 serves as half of the pathway through which the actuation wires 20, 22, the central lumen of the body 12 (if any), and the wires leading to the electrodes 18 pass on their way to the proximal end 26 of the handle 14 (the distal groove 66 in the upper grip portion 28 would serve as the other half of said pathway). Likewise, the proximal groove 68 serves as half of the pathway through which the central lumen of the body 12 and the wires leading to the electrodes 18 pass on their way to the proximal end 26 of the handle 14 (the proximal groove 68 in the upper grip portion 28 would serve as the other half of said pathway).

As shown in FIG. 3, a pair of oblique walls 70, 72 obliquely converge towards the longitudinal centerline L of the lower grip portion 30 and extend generally perpendicularly upwards from the recessed planar area 60 to the distal planar area 62. The oblique walls 70, 72 serve as an abutment for the linear side or edge 44 of the actuator 32 to prevent the actuator from over pivoting relative to the grip portions 28, 30. In other words, the oblique walls 70, 72 serve as mechanical stops to limit movement of the actuator 32 in opposite directions from the actuator's central undeflected position depicted in FIGS. 1 and 2.

As illustrated in FIG. 3, in one embodiment, a pivot 74 extends generally perpendicularly from the recessed planar area 60 in a location that is near the convergence of the oblique walls 70, 72. The pivot 74 is a cylindrical member that is received within the pivot holes 48, 50 of the actuator 32 (see FIG. 2) and serves as a pivot about which the actuator 32 may pivot. In one embodiment, the axis of the pivot 74 is centered along the longitudinal centerline L of the lower grip portion 30, and the pivot 74 includes a pivot groove 76 that is aligned with the longitudinal centerline L in manner similar to that described with respect to the distal and proximal grooves 66, 68. When the upper and lower grip portions 26, 38 are matingly joined together, the end planar surface of the upper grip portion's pivot matingly abuts against the end planar surface of the lower grip portion's pivot 74.

As shown in FIG. 3, in one embodiment, a wire guide or tube 52 extends from the distal groove 66 to, and through, the pivot groove 76. The wire guide 52 serves to maintain the actuation wires 20, 22 in an alignment that is generally parallel with the longitudinal centerlines L of the grip portions 36, 38. As illustrated in FIG. 3, a space exists between the wire guide 52 and the recessed planar area 60. Thus, as previously mentioned, the portion of the bottom plate 38 that defines the most proximal edge of the pivot hole 50 may displace through the space between the wire guide 52 and the recessed planar area 60 when the actuator 32 pivots about the pivot 74. A similar configuration exists between the wire guide 52 and the recessed planar area of the upper grip portion 28 for accommodating the displacement of the portion of the top plate 36 that defines the most proximal edge of the pivot hole 48 when the actuator 32 pivots about the pivot 74.

As illustrated in FIG. 3, a pair of peripheral walls 78, 80 extend from the proximal planar area 64 along the side edges of the proximal portion of the recessed planar area 60. As indicated in FIG. 3, to define a gap 82 (see FIG. 1) between the upper and lower grip portions 28, 30 through which the actuator 32 may laterally displace relative to the grips 28, 30 when the grips 28, 30 are mated together, the peripheral walls 78, 80 do not extend along the full length of the side edges of the recessed planar area 60.

As shown in FIG. 3, a pair of bearing assemblies 90, 92 are located between the peripheral walls 78, 80 in the proximal portion of the recessed planar area 60. Each bearing assembly 90, 92 is positioned on an opposite side of the longitudinal centerline L of the lower grip portion 30. As illustrated in FIG. 3, the bearing assemblies 90, 92 serve to divert the actuation wires 20, 22 from an orientation that is generally parallel to the centerlines L of the grip portions 28, 30 to an orientation that is generally non-parallel (e.g., oblique and/or perpendicular) to the centerlines L as the actuation wires 20, 22 extend through the distal groove 66, through the wire guide 52, about the respective bearing assemblies 90, 92 and out to their respective points of connection to the actuator 32.

As indicated in FIG. 3, each bearing assembly 90, 92 includes an upper annulus shaped bearing 94, 96 and a lower annulus shaped bearing coaxially rotateably mounted on an axle 98, 100 and separated from each other by a wire divider 54, 56. In one embodiment, the axles 98, 100 are generally perpendicular to the longitudinal centerline L and the recessed planar area 60. The upper extreme ends of each axle 98, 100 extend upward into receiving holes in the recessed planar area of the upper grip portion 36. Similarly, the lower extreme ends of each axle 98, 100 extend downward into receiving holes in the recessed planar area 60 of the lower grip portion 38. Thus, each bearing assembly 90, 92 with its respective upper bearing 94, 96, lower bearing, and wire divider 54, 56 is held in place as an integral unit within the gap 82 defined between the upper and lower grip portions 36, 38. As can be understood from FIG. 3, the arrangement of the annulus shaped upper bearings 94, 96 and their respective axles 98, 100 is a mirror image of the annulus shaped lower bearings and their respective axles 98, 100.

As illustrated in FIG. 2, the bearing assemblies 90, 92 are positioned such that the portions of the wire dividers 54, 56 that are located distal to the annulus shaped bearings 94, 96 extend into the slot 53, and the annulus shaped bearings 94, 96 are located proximal to the arcuate side 46 of the actuator 32. In other words, in one embodiment, the distal portions of the wire dividers 54, 56 extend into the slot 53. As a result, the top and bottom plates 36, 38 displace over and under, respectively, the distal portions of the wire dividers 54, 56 as the actuator 32 pivots about the pivot 74.

As shown in FIG. 3, each wire divider 54, 56 is elongated and has smooth edges or contoured surfaces to prevent abrasion of the actuation wires 20, 22 as they displace against the wire dividers 54, 56. In one embodiment, the wire dividers 54, 56 have an elliptical shape with the major axis parallel to the longitudinal centerlines L of the grip portions 36, 38. The wire dividers 54, 56 elevationally separate the actuation wires 20, 22 into generally parallel planes as the actuation wires 20, 22 cross over each other when being diverted about their respective bearing assemblies 90, 92.

As can be understood from FIG. 3, the actuation wires 20, 22 enter the handle 14 from the body 12 and travel through the distal groove 66 and the wire guide 52 in substantially one plane. The actuation wires 20, 22 begin to separate into parallel planes as they proceed towards the wire dividers 54, 56. As the actuation wires 20, 22 proceed about the bearing surfaces of the lower and upper bearings 94, 96, the first actuation wire 22 passes against the top surface of the wire dividers 54, 56, and the second actuation wire 20 passes against the bottom surface of the wire dividers 54, 56.

As indicated in FIGS. 1-3, in one embodiment, the actuation wires 20, 22 enter the handle 14 from the body 12 and extend through the distal groove 66 and the wire guide 52 in an orientation that is generally parallel to the centerlines L of the grip portions 28, 30. As illustrated in FIG. 3, in one embodiment, as the actuation wires 20, 22 exit the wire guide 52 on their way to their respective bearing assemblies 90, 92, the actuation wires 20, 22 begin to diverge away from each other. Also, as indicated in FIG. 2, as the actuation wires 20, 22 pass through the wire guide 52 and on to their respective bearing assemblies 90, 92, the actuation wires 20, 22 pass through the actuator 32 (i.e., through the slot 53 defined by the top and bottom plates 36, 38).

As shown in FIG. 3, in one embodiment, a first actuation wire 22 extends from the wire guide 52, passes over a first wire divider 56, and first encounters a first upper bearing 96 on the side of the first upper bearing 96 that is on the opposite side of the first upper bearing's axle 100 from the longitudinal centerline L of the lower grip portion 30. The first actuation wire 22 then extends about the first upper bearing 96 (thereby changing from an orientation that was generally parallel to the centerline L to an orientation that is non-parallel, e.g., oblique and/or perpendicular, to the centerline L) and passes against the second upper bearing 94 as the first actuation wire 22 passes between the two upper bearings 94, 96 on the first actuation wire's way to its point of connection to the actuator 32. On the first actuation wire's way to its point of connection with the actuator 32 (after leaving the second upper bearing 94) the first actuation wire 22 again passes through the slot 53 and connects to the actuator 32 near an extreme outer end of a first rib 40 (see FIG. 2).

As can be understood from FIG. 3, in a manner similar to that just described, the second actuation wire 20 extends from the wire guide 52, passes below the second wire divider 54, and first encounters a first lower bearing on the side of the first lower bearing that is on the opposite side of the first lower bearing's axle 98 from the longitudinal centerline L of the lower grip portion 30. The second actuation wire 20 then extends about the first lower bearing (thereby changing from an orientation that was generally parallel to the centerline L to an orientation that is generally non-parallel, e.g., oblique and/or perpendicular, to the centerline L) and passes against the second lower bearing as the second actuation wire 20 passes between the two lower bearings on the second actuation wire's way to its point of connection to the actuator 32. On the second actuation wire's way to its point of connection with the actuator 32 (after leaving the second lower bearing) the second actuation wire 20 again passes through the slot 53 and connects to the actuator 32 near an extreme outer end of a second rib 42 (see FIG. 2).

As can be understood from the FIG. 3 and the immediately preceding description, in one embodiment, each actuation wire 20, 22 starts on a first side of the longitudinal centerline L as the actuation wire 20, 22 travels along the distal groove 66 and the wire guide 52 on its way to its respective bearing assembly 90, 92. However, once each actuation wire 20, 22 encounters its respective bearing assembly 90, 92, the actuation wire 20, 22 is diverted such that the actuation wire 20, 22 passes onto the other side of the longitudinal centerline L. This embodiment is advantageous because it maximizes the extent to which the actuation wires 20, 22 can be displaced by the actuator.

In other embodiments where less actuation is required, the actuation wires 20, 22 will not pass from one side of the longitudinal centerline L to the other as the actuation wires 20, 22 are diverted about their respective bearing assemblies 90, 92. For example, where the first actuation wire 22 is extended between the upper bearings 94, 96 prior to routing about the first upper bearing 96, and the second actuation wire 20 is extended between the lower bearings prior to routing about the first lower bearing, the actuation wires 20, 22 will not cross the longitudinal centerline L.

In use, the body 12 is inserted into the patient in a manner well known in the art. An operator grasps the handle 14 and manipulates the actuator 32 between his thumb and finger. Advantageously, the actuator 32 protrudes from each side of the handle 14 to allow for such ease of movement and manipulation. The actuator 32 is moved relative to the handle 14, which causes the actuation wires 20, 22 to be displaced about the bearing assemblies 90, 92. As a result, the distal portion 16 of the body 12 deflects.

Although the present invention has been described with reference to preferred embodiments, persons skilled in the art will recognize that changes may be made in form and detail without departing from the spirit and scope of the invention. The invention is limited only by the scope of the following claims.

What is claimed is:

1. A catheter actuation handle for deflecting a distal end of a tubular catheter body having first and second actuation wires extending from a proximal end of the body, the handle, comprising:
    a first grip portion including a pivot with a pathway extending through the pivot and generally parallel to a longitudinal centerline of the first grip portion;
    a bearing assembly located on the first grip portion proximal to the pivot; and
    an actuator pivotally coupled to the pivot and including first and second ends that are laterally offset from the longitudinal centerline and are on opposite sides of the centerline from each other,
    wherein, when a distal end of the handle is coupled to the proximal end of the body, the first and second actuation wires extend along the pathway to the bearing assembly and the bearing assembly diverts the first actuation wire to a first connection point on the actuator and the second actuation wire to a second connection point on the actuator.

2. The handle of claim 1, wherein the first connection point is near the first end and the second connection point is near the second end.

3. The handle of claim 1, wherein the bearing assembly changes the orientation of the actuation wires from an orientation that is generally parallel to the longitudinal centerline to an orientation that is generally non-parallel to the longitudinal centerline.

4. The handle of claim 3, wherein the non-parallel orientation is oblique.

5. The handle of claim 3, wherein the non-parallel orientation is generally perpendicular.

6. The handle of claim 1, wherein the actuation wires cross the longitudinal centerline as they divert about the bearing assembly and travel to their respective connection points on the actuator.

7. The handle of claim 1, wherein the first grip portion further includes a first generally planar area from which the pivot extends generally perpendicularly.

8. The handle of claim 7, wherein the actuator further includes a first plate that is displaceable through a first space defined between the first generally planar area and a longitudinal axis of the pathway.

9. The handle of claim 8, further comprising a second grip portion mated with the first grip portion and including a second generally planar area.

10. The handle of claim 9, wherein the actuator further includes a second plate that is coupled to the first plate and is displaceable through a second space defined between the second generally planar area and the longitudinal axis of the pathway.

11. The handle of claim 1, wherein the actuator further includes first and second generally parallel plates that define a slot through which the actuation wires pass as the actuation wires extend from the pathway to the bearing assembly.

12. The handle of claim 11, wherein the bearing assembly further includes a portion that extends into the slot.

13. The handle of claim 1, wherein the bearing assembly further includes a first bearing positioned on a first side of the longitudinal centerline and a second bearing positioned opposite longitudinal centerline from the first bearing.

14. The handle of claim 13, wherein the bearings are annulus shaped.

15. The handle of claim 13, wherein the first actuation wire diverts about the first bearing and the second actuation wire diverts about the second bearing.

16. The handle of claim 15, wherein the bearing assembly further includes a separating assembly for separating the actuation wires into separate planes and the bearings are on opposite sides of the separating assembly from each other.

17. The handle of claim 15, wherein the actuation wires cross the longitudinal centerline as they extend from their respective bearings to their respective connections points.

18. A catheter actuation handle for deflecting a distal end of a tubular catheter body having first and second actuation wires extending from a proximal end of the body, the handle, comprising:
    a grip portion including a pivot and a longitudinal centerline;
    a bearing assembly located on the grip portion proximal to the pivot; and an actuator pivotally coupled to the pivot and including first and second ends that are laterally offset from the longitudinal centerline and are on opposite sides of the centerline from each other, wherein, when a distal end of the handle is coupled to the proximal end of the body, the first and second actuation wires extend along the grip portion towards the bearing assembly in a first orientation that is generally parallel to the longitudinal centerline, wherein the bearing assembly is adapted to change the first orientation to a second orientation that is generally non-parallel to the longitudinal centerline as the bearing assembly diverts the first actuation wire to a first connection point on the actuator and the second actuation wire to a second connection point on the actuator.

19. The handle of claim 18, wherein the non-parallel orientation is oblique.

20. The handle of claim 18, wherein the non-parallel orientation is generally perpendicular.

21. The handle of claim 18, wherein the first connection point is near the first end and the second connection point is near the second end.

22. The handle of claim 18, wherein the actuation wires cross the longitudinal centerline as they divert about the bearing assembly and travel to their respective connection points on the actuator.

23. The handle of claim 18, wherein the actuator further includes first and second generally parallel plates that define a slot through which the actuation wires pass as the actuation wires extend along the grip portion towards the bearing assembly.

24. The handle of claim 23, wherein the bearing assembly further includes a portion that extends into the slot.

25. The handle of claim 18, wherein the bearing assembly further includes a first bearing positioned on a first side of the longitudinal centerline and a second bearing positioned opposite longitudinal centerline from the first bearing.

26. The handle of claim 25, wherein the bearings are annulus shaped.

27. The handle of claim 25, wherein the first actuation wire diverts about the first bearing and the second actuation wire diverts about the second bearing.

28. The handle of claim 27, wherein the bearing assembly further includes a separating assembly for separating the actuation wires into separate planes and the bearings are on opposite sides of the separating assembly from each other.

29. A method of deflecting a distal end of a tubular catheter body having first and second actuation wires and coupled at a proximal end to an actuation handle, the method comprising:

diverting the first and second actuation wires about a bearing assembly of a grip portion of the handle, wherein the orientation of each actuation wire changes from a first orientation that is generally parallel to a longitudinal centerline of the grip portion to a second orientation that is generally non-parallel to the longitudinal centerline; and pivoting an actuator about a pivot of the grip portion, wherein the pivot is distal to the bearing assembly, to place the first actuation wire into tension.

30. The method of claim 29, wherein the non-parallel orientation is oblique.

31. The method of claim 29, wherein the non-parallel orientation is generally perpendicular.

32. The method of claim 29, further including routing the first and second actuation wires through a pathway in the pivot, wherein the pathway is generally parallel to the longitudinal centerline.

33. The method of claim 29, further comprising routing the actuation wires through a slot defined in the actuator after leaving the proximal end of the body, but prior to reaching the bearing assembly.

34. The method of claim 33, further comprising routing the actuation wires through the slot after leaving the bearing assembly for the actuator.

35. The method of claim 29, further comprising causing each actuation wire to cross from one side of the longitudinal centerline to another when diverting the actuation wires about the bearing assembly.

36. A method of manufacturing a catheter with an actuation handle, the method comprising:

providing a grip portion of the handle with a pivot;
forming in the pivot a pathway that is generally parallel with a longitudinal centerline of the grip portion;
placing a bearing assembly on the grip portion proximal to the pivot;
pivotally mounting an actuator on the pivot; and
routing first and second actuation wires through the pathway, about the bearing assembly, and to the actuator.

37. The method of claim 36, further comprising changing the actuation wires from a first orientation that is generally parallel to the longitudinal centerline to a second orientation that is non-parallel to the centerline when routing the actuation wires about the bearing assembly.

38. The method of claim 37, wherein the non-parallel orientation is oblique.

39. The method of claim 37, wherein the non-parallel orientation is generally perpendicular.

40. The method of claim 36, further comprising causing each actuation wire to cross from one side of the longitudinal centerline to another when routing the actuation wires about the bearing assembly.

41. The method of claim 36, further comprising routing the actuation wires from the pathway to the bearing assembly in a slot defined in the actuator.

* * * * *